United States Patent [19]

Wan

[11] Patent Number: 4,497,967
[45] Date of Patent: Feb. 5, 1985

[54] PROCESS FOR THE PREPARATION OF ETHANOL FROM METHANOL, CARBON MONOXIDE AND HYDROGEN

[75] Inventor: Chee-Gen Wan, Fort Lee, N.J.

[73] Assignee: The Halcon SD Group, Inc., New York, N.Y.

[21] Appl. No.: 621,271

[22] Filed: Jun. 15, 1984

[51] Int. Cl.³ .......................................... C07C 29/136
[52] U.S. Cl. .................................. 568/885; 260/549; 560/265
[58] Field of Search ....................... 568/885; 560/265; 260/549

[56] References Cited

U.S. PATENT DOCUMENTS 3,260,683 7/1966 Endler .................................. 568/885
4,046,807 9/1977 Kuckertz ............................ 260/549
4,454,358 6/1984 Kummer et al. ..................... 568/885

FOREIGN PATENT DOCUMENTS 1286040 1/1969 Fed. Rep. of Germany ...... 560/265

Primary Examiner—J. E. Evans
Attorney, Agent, or Firm—William C. Long; Riggs T. Stewart; Daniel R. Zirker

[57] ABSTRACT

An integrated process for the preparation of ethanol from methanol, carbon monoxide and hydrogen feedstock is disclosed; the process featuring the steps of esterifying methanol and acetic acid to form methyl acetate; carbonylating the methyl acetate to form acetic anhydride; esterifying acetic anhydride with a lower aliphatic alcohol in an anhydrous zone to form the corresponding aliphatic acetate; hydrogenating the aliphatic acetate in a second anhydrous zone to form ethanol and the corresponding aliphatic alcohol; and separating the formed ethanol stream into an ethanol product stream and/or aliphatic alcohol recycle stream, which is recycled to react with acetic anhydride.

7 Claims, 1 Drawing Figure

PROCESS FOR THE PREPARATION OF ETHANOL FROM METHANOL, CARBON MONOXIDE AND HYDROGEN

BACKGROUND OF THE INVENTION

This invention is related to the preparation of ethanol, and more particularly is related to a process for producing ethanol through an integrated series of catalytic process operations which form ethanol from a methanol, carbon monoxide and hydrogen feedstock.

Ethanol is a well known industrial chemical which has been produced in great volume for many years, for a variety of usages.

A number of processes are known in the art for reacting methanol with carbon monoxide and hydrogen in the presence of a variety of catalyst systems to produce ethanol. However, most of these processes suffer from a number of major flaws, such as producing a large number of unwanted co-products, and being uneconomical for industrial operation.

Thus, it is an object of this invention to provide a novel, effective and economic process for producing ethanol, wherein the feedstock materials comprise only methanol, carbon monoxide and hydrogen.

SUMMARY OF THE INVENTION

In accordance with the invention, an integrated cyclic process is disclosed for the preparation of ethanol from methanol, carbon monoxide and hydrogen feedstocks, comprising the steps of reacting methanol and acetic acid streams, the acetic acid preferably being recycled from a subsequent zone of the process, in a first esterification zone to form methyl acetate; reacting the formed methyl acetate with carbon monoxide in a carbonylation zone to form acetic anhydride; reacting the formed acetic anhydride with at least one lower aliphatic alcohol, preferably ethanol, which is recycled from a downstream hydrogenation zone, in a substantially anhydrous second esterification zone to form the corresponding lower aliphatic acetates, preferably ethyl acetate, and acetic acid; reacting the formed lower aliphatic acetates, preferably ethyl acetate, with hydrogen in a substantially anhydrous hydrogenation zone to form both ethanol and also the corresponding aliphatic alcohols from the acetates, if the preferred ethyl acetate, is not the chosen acetate; separating the formed alcohol into a first ethanol product stream, and a second comprising the formed corresponding aliphatic alcohol, recycled to the second esterification zone to form the corresponding aliphatic acetate and acetic acid. The process can be either continuous or batch, preferably continuous, and is conducted at effective temperatures and pressures in the presence of effective catalysts and promoters.

DETAILED DESCRIPTION OF THE INVENTION

Figure 1:
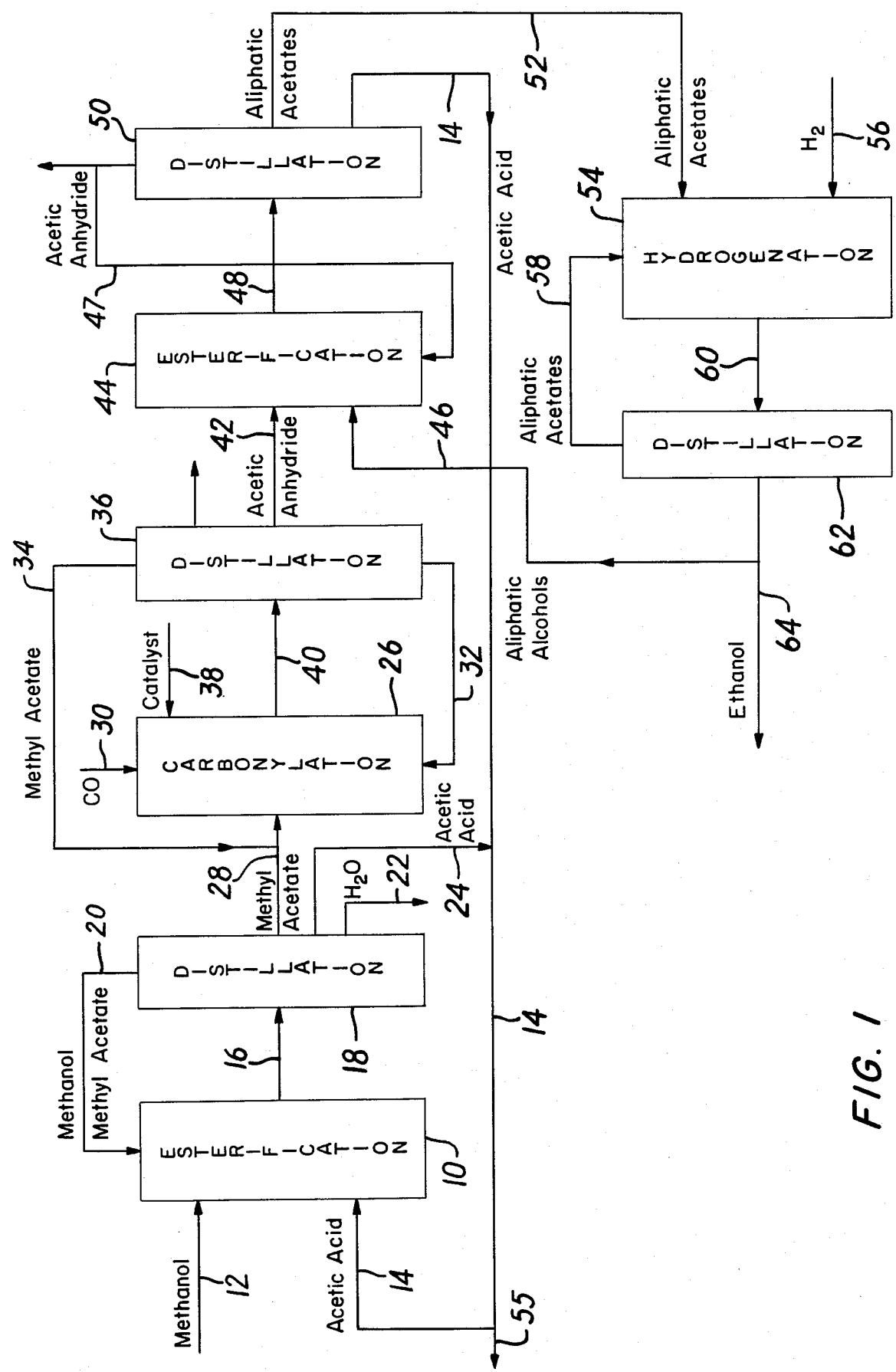

The process of this invention will be more readily understood by reference to the accompanying FIGURE which discloses, solely for purposes of simple explanation, a preferred reaction system for carrying out the process of this invention. Thus, referring to the drawing, the reference numeral 10 represents a first esterification zone, which may comprise one or more reactors of any particular type known to those skilled in the art, and into which are fed methanol and acetic acid feed streams, together with a recycle stream and which further contains a suitable esterification catalyst. Thus methanol, in pure or diluted form, is supplied through line 12 and the acetic acid stream 14, which is preferably formed as a recycled product of at least one subsequent substantially anhydrous distillation occurring at a downstream esterification operation, is passed to the first esterification zone 10 where it is contacted and mixed with methanol in the presence of a suitable esterification catalyst. The esterification of acetic acid by methanol is a well known reaction which can be catalyzed by a variety of catalysts which are acidic in nature, such as sulfuric acid, i.e., Fischer esterification. It is preferred, however, to use a solid catalyst such as an acid-reacting ion exchange resin, wherein the resin is positioned in the esterification zone through which the feedstock materials are passed and contacted. Esterification catalysts of this type are well known, and representative catalysts are described, for example, in U.S. Pat. Nos. 2,980,731 and 3,278,585. Typical esterification temperatures of about 50° to 160° C. are employed and superatmospheric pressures of about 30 to 200 psig; lower or higher pressures can be employed if so desired. For best results residence times of the order of 5 to 50 minutes are maintained. Although the esterification reaction will theoretically consume equal molar parts of acetic acid and methanol, it is desired that an excess of either one of the reactants be present, e.g., about 50 to 250% excess based upon the other reactant, with most preferably the acetic acid being in excess. Such a system is readily accomplished by recycling the reactant through the system, i.e., recovering it from the esterification effluent and recycling it back to the esterification zone.

The effluent from first esterification zone 10 will typically comprise product methyl acetate, co-product water, together with unreacted acetic acid and methanol. This stream leaves esterification zone 10 through line 16 and enters distillation zone 18 where it is readily separated in conventional manner through a series of fractional distillations. Typically, the mixture is first distilled at a temperature of 40° to 130° C. and at a pressure of 10 to 20 psia to produce as a distilled product a methanol-methyl acetate azeotrope from the remaining methyl acetate, acetic acid and water, which is recycled through line 20 back to esterification zone 10. Thus, the methanol-methyl acetate azeotrope is conveniently returned to the esterification zone for subsequent reaction with acetic acid, while the remaining methyl acetate is, in accordance with the invention, supplied as a feed stream to the carbonylation zone, most preferably after a dehydration stage to remove any accompanying water, and which exits through line 22 from the system. Dehydration can be effected in any conventional manner, e.g., such as by solvent extraction as set forth in U.S. Pat. No. 3,904,676. The wet acetic acid recovered as bottoms from this distillation zone is preferably distilled at temperatures of about 40° to 160° C. and at atmospheric pressure to dehydrate the acetic acid, which is then recycled to the first esterification zone through lines 24 and 14 for subsequent conversion to methyl acetate.

Reference numerical 26 designates a carbonylation zone, which may comprise one or more pressure reactors of any convenient type, into which is fed methyl acetate stream 28 from distillation zone 18, together with carbon monoxide feed stream 30 supplied from a suitable source, as well as recycle stream 32 which preferably also contains an effective carbonylation catalyst, typically one comprising a metal of Group VIII of the Periodic Table in combination with iodine or bromine moieties, preferably in a liquid phase system. The carbon monoxide, in pure or diluted form, enters through line 30, the methyl acetate enters through both line 28 and line 34, the latter a recycle from distillation zone 36, and the catalyst, if removed with the reaction effluent, is recycled, as will be later described, through line 32, while additional fresh catalyst components can also be supplied, if desired, through line 38. Thus the carbonylation reaction can be undertaken in a batch operation if so desired, but it is preferred, particularly for commercial reasons, to operate in a continuous mode, as is true for all the steps of the instant process. Carbonylation can be typically carried out at temperatures of 20° to 500° C., and preferably 100° to 300° C. under a carbon monoxide partial pressure ranging from 0.1 to 15,000 psi.

After exiting carbonylation zone 26 the reaction mixture passes through line 40 and enters distillation zone 36 where it can be conventionally separated into its principal components. Distillation zone 36 can also be defined by one or more distillation units, e.g., flash and/or fractional distillation apparatus, as is apparent to those skilled in the art. If the carbonylation zone is operated entirely in the liquid phase, the entire reaction mixture, including the Group VIII catalyst, is removed for subsequent separation. However, if the carbonylation is carried out in a boiling reactor, the effluent will be in the vapor phase and the relatively non-volatile catalyst will remain in the boiling liquid body of the carbonylation zone. The low boiling components of the mixture, including methyl acetate, methyl iodide and the like are removed through line 34 and, preferably, are at least partially recycled through line 34 to line 28 and back to carbonylation zone 26 or, alternatively, directly to zone 26. The higher boiling components remaining, including the essentially non-volatile catalyst components, are recycled to carbonylation zone 26 via line 32 while the desired product acetic anhydride is removed from the distillation zone via line 42 and passes into second esterification zone 44. A portion of the exiting acetic anhydride stream can be diverted for use in the esterification reaction to form methyl acetate, which is then used as feed for the carbonylation reaction, or, taken off as a co-product of the process, if desired.

As earlier mentioned, the carbonylation reaction involving methyl acetate and carbon monoxide which is carried out in carbonylation zone 26 is facilitated by the presence of a catalyst, most suitably a Group VIII metal, for example, a Group VIII noble metal, i.e., rhodium, iridium, ruthenium, palladium, osmium and platinum, as disclosed in Belgian Pat. Nos. 819,455 and 839,322, or a nickel catalyst as described in U.S. Pat. Nos. 4,002,677 and 4,022,678. The disclosures of these two U.S. patents are incorporated herein by reference. Thus, in the case of a Group VIII noble metal catalyst the Group VIII noble metal can be employed in any convenient form, viz. in the zero valent state or in any higher valent form. The amount of Group VIII noble metal catalyst is in no way critical and can vary over a wide range.

The carbon monoxide feed is preferably employed in substantially pure form, as is available commercially, but inert diluents such as carbon dioxide, nitrogen, methane and the noble gases can be present if desired. The presence of inert diluents does not effect the carbonylation reaction but their presence makes it necessary to increase the total pressure in order to maintain the desired CO partial pressure. The carbon monoxide, like the other reactants, should, however, be essentially dry, i.e., the CO and the other reactants should be reasonably free from water.

It has been previously found that the activity of the Group VIII noble metal catalysts described above can be significantly improved, particularly with respect to reaction rate and product concentration, by the concurrent use of a promoter. Effective promoters are those disclosed in the U.S. Pat. No. 4,234,719 and include the elements having atomic weights greater than 5 of Groups IA, IIA, IIIA, IVB, VIB, the non-noble metals of Group VIII and the metals of the lanthanide and actinide groups of the Periodic Table. Particularly preferred are the lower atomic weight metals of each of these groups, e.g. those having atomic weights lower than 100, and especially preferred are metals of Groups IA, IIA and IIIA as are metals of Group VIB and the non-noble metals of Group VIII.

The activity of the Group VIII noble metal catalysts described above is also significantly improved, particularly with respect to reaction rate and product concentration, catalyst stability and corrosion inhibition, by the concurrent use as disclosed in U.S. Pat. No. 4,234,719 of a promoter combination or co-promoter system containing a metal component which is a metal of Groups IVB, V and VIB, and the non-noble metals of Group VIII, in any of the forms described above, in association or combination with an organo-nitrogen compound or an organo-phosphorous compound wherein the nitrogen and the phosphorous are trivalent.

In accordance with a preferred embodiment of the invention, the carbonylation operation is carried out in a single reaction zone to which a halide source, e.g., a hydrocarbyl halide such as methyl iodide, and the methyl acetate are both charged and are heated together, preferably in the liquid phase, in the presence of carbon monoxide and in the presence of the Group VIII metal catalyst. It will be understood that the hydrocarbyl halide may be formed in situ and the halide may thus be supplied to the system not only as the hydrocarbyl halide but the halogen moiety may also be supplied as another organic halide, or, as the hydro-halide or other inorganic halide, e.g. salts, such as the alkali metal or other metal salts, or even as elemental iodine or bromine.

As previously mentioned, in carrying out the carbonylation steps of the invention, a wide range of temperatures, e.g. 20° to 500° C. are suitable but temperatures of 100° to 300° C. are preferably employed and the more preferred temperatures generally lie in the range of 125° to 250° C. The time of reaction is also not a parameter of the process and depends largely upon the temperature employed, but typical residence times, by way of example, will generally fall in the range of 0.1 to 20 hours. The reaction is carried out under superatmospheric pressure, but excessively high pressures, which require special high-pressure equipment, are not necessary. Typically, total pressures up to about 3,000 psi are used but most preferably they are at most about 1,000 psi. The reaction can be advantageously carried out in an autoclave or similar apparatus.

The effluent 40 from the carbonylation step is separated, e.g., distilled, by conventional techniques to separate the desired product, anhydrous acetic anhydride, and to recover streams containing unreacted methyl acetate, iodine moieties, catalyst components (and promoter components if employed), all of which are recycled to the carbonylation reactor for reuse. As indicated above, the distillation of the carbonylation effluent is conveniently effected in one or more distillation units, e.g., flash and/or fractional distillation devices. In distillation zone 36 temperatures of 50° to 180° C. and pressures of 0.1 to 60 psi typically prevail.

Reference number 44 represents a second esterification zone which may comprise one or more reactors of any particular type known to those skilled in the art, and into which the bulk of the acetic anhydride in line 42 proceeds. Inside the esterification zone the acetic anhydride is mixed with a feed stream 46 comprising at least one lower aliphatic alcohol, preferably ethanol, and a recycled stream 47 which contains acetic anhydride, acetic acid and, optionally, an effective esterification catalyst. Suitable lower aliphatic alcohols for the process of this invention as feed into the second esterification zone can comprise any $C_1$-$C_{10}$ branched or straight chain aliphatic alcohol, and, more commonly, methanol, ethanol and propanol. Ethanol is the most preferred aliphatic alcohol. Thus, acetic anhydride, in either pure or diluted anhydrous form, is passed through line 42 and at least one lower aliphatic alcohol, e.g., ethanol, containing feed stream 46, which, preferably, is a product of a substantially anhydrous downstream distillation occurring in conjunction with a downstream hydrogenation stage, is passed into esterification zone 44 whereupon it is contacted and mixed with stream 42 and recycle stream 47. The esterification of acetic anhydride by ethanol or methanol is a well known reaction which preferably is catalyzed by a variety of catalysts that are acidic in nature, and which are known to those in the art. It is preferred to use a catalyst such as an acid-reacting resin wherein the resin is positioned in the esterification zone through which the reactant materials are passed and contacted. Typical esterification temperatures of about 50° to 140° C. are employed along with moderate pressures; however, lower or higher pressures can be employed if so desired. For best results residence times of the order of 10 to 100 minutes are maintained. Although the esterification reaction will theoretically consume equal molar parts of acetic anhydride and aliphatic alcohol, it is desired that an excess of either one of the reactants be present, e.g., about 50 to 400% excess acetic anhydride in acetic acid solution. The reaction is readily carried out by continually recycling the reactant through the system, i.e., by recovering it from the esterification effluent and recycling it back to the esterification zone 44 through line 47.

A critical parameter in the process of the invention is the requirement of substantially anhydrous operation in the second esterification zone 44, as well as in the adjacent hydrogenation zone 54, together with their accompanying distillation and other product separation units. Anhydrous operation is particularly desirable since it greatly minimizes any corrosion damage occurring within the system and also permits the utilization of a simplified separation procedure, due to the substantial absence of water from the reaction mixture. Such benefits substantially compensate for the increased expense necessitated through the utilization of an acetic anhydride feed stream to the esterification zone 44.

The effluent stream 48 from the second esterification zone 44 will typically comprise the formed lower aliphatic acetates, e.g., methyl and/or ethyl acetate, and acetic anhydride, together with acetic acid and some unreacted alcohol. This stream leaves the esterification zone and passes into a suitable separation zone, i.e., distillation zone 50, whereupon it is readily separated in a conventional manner through a series of fractional distillations. Typically, the mixture is first distilled at a temperature of 50° to 150° C. and at a pressure of 0.1 to 30 psi to produce a primary distillate product stream of the preferred ethyl acetate or other lower aliphatic acetate, which is withdrawn and passed through line 52, into hydrogenation zone 54, as the feed stream for the hydrogenation reaction undertaken therein. The remaining mixture of acetic anhydride and acetic acid is recycled back to esterification zone 44 through line 47, together with any aliphatic alcohols and acetates present. The acetic acid recovered as a co-product of this distillation is preferably distilled at temperatures of about 60° to 150° C. and approximately atmospheric pressures, exiting the distillation zone through line 14 and is preferably recycled back to first esterification zone 10 to be used as a feed stream where it is reacted with methanol; however, if desired, some of the acetic acid can also be withdrawn through line 55 as product.

Reference number 54 represents a hydrogenation zone, which may comprise one or more reactors of any particular type known to those skilled in the art and which insures satisfactory contact between the feedstocks, catalyst and hydrogen. The bulk of the aliphatic acetate, e.g. ethyl acetate, passes through line 52 into zone 54 where it is mixed together with a hydrogen stream 56 which is, preferably, employed in substantially pure form such as is available commercially, but inert diluents such as carbon dioxide, nitrogen, methane and the like can be present if desired. The presence of such inert diluents does not affect the hydrogenation reaction but their presence makes it necessary to increase the total pressure in order to maintain the desired $H_2$ partial pressure. The hydrogen should be essentially anhydrous, although minor amounts of water such as may be found in the commercial forms of the reactants is acceptable. The recycled aliphatic acetate stream 58 in the vapor phase is also passed into hydrogenation zone 54. The acetate and hydrogen feed streams are passed into the hydrogenation zone 54, whereupon they are contacted and reacted in the presence of a suitable hydrogenation catalyst, or, mixture of catalysts. The hydrogenation of aliphatic acetates is a well known reaction which can be catalyzed by any of a variety of catalysts which are well known to those in the art, such as those described in U.S. Pat. Nos. 2,079,414, 4,113,662 and 2,782,243, preferably copper chromite.

Hydrogenation may be carried out at elevated temperatures and hydrogen pressures in a conventional pressure reactor. The hydrogenation may be carried out, depending largely upon catalyst concentration, by using hydrogen pressures ranging from 0.1 to 1500 psi and at temperatures ranging from 75° to 300° C. Higher pressures and temperatures may be used if so desired, but usually it is desirable to employ pressures ranging from 300 to 1000 psi, or, employ temperatures substantially higher than 250° C., as long as an industrially acceptable rate of reaction is maintained. The hydrogenation may be carried out in a continuous manner, such as by contacting a mixture of the catalyst, the feed and the recycled aliphatic acetate streams under a hydrogen atmosphere at suitable pressures in the presence of an effective activated catalyst. The catalyst may be recovered after the hydrogenation is completed and may also be reactivated if so desired by procedures known to those skilled in the art. Although the hydrogenation reaction will theoretically consume two molar parts of hydrogen per part acetate, it is desired that an excess of hydrogen be present, e.g., about 2 to 60 moles of hydrogen per mole of ester is most preferred. The reaction is readily accomplished by additionally recycling the reactants throughout the system, i.e., by recovering the unreacted aliphatic acetates from the distillation effluent and recycling them back through line 58 into the hydrogenation zone 54. As in the case of the second esterification zone 44 operation, it is critical that substantially anhydrous conditions prevail in the hydrogenation zone as well as in the accompanying distillation and other necessary separation units.

The effluent product from the hydrogenation zone 54 will typically comprise ethanol and other aliphatic alcohols corresponding to the acetates used, if not ethyl acetate, together with any unreacted aliphatic acetates, hydrogen and various byproducts. This stream leaves the hydrogenation zone through line 60 and enters into a suitable separation zone, i.e., distillation zone 62, whereupon it is readily separated in conventional manner through a series of fractional distillations. Typically, if ethyl acetate is used, the mixture is first distilled at a temperature of 40° to 140° C. and at pressures of 0.1 to 40 psi to produce as the primary distilled product an ethanol stream which is withdrawn through line 64, and preferably a desired amount is recycled through line 46 as feed for second esterification zone 44, to undertake the anhydrous esterification reaction with acetic anhydride with the remainder of the ethanol being taken off as product. The ethyl acetate recovered from the distillation zone is preferably recycled back through line 58 to the hydrogenation zone and again reacted with hydrogen. If at least one other aliphatic acetate, other than ethyl acetate, is used, the separation procedure is similar but depends on whether the corresponding aliphatic alcohol is lighter or heavier than the ethanol product. The separated aliphatic alcohol or alcohols are recycled through line 46 as feed for the second esterification zone 44.

EXAMPLE

Using an apparatus system such as illustrated in the drawing, esterification zone 10, which is suitably defined by a tank which contains a bed of acidic ion-exchange resins (Dowex 50W) and is operated at about 70° C. and 120 psia, is fed with 260 parts per hour of methanol, and a recycle stream containing 50 parts per hour of a methanol-methyl acetate azeotropic mixture (line 20). The acetic acid feed of 260 parts per hour to the esterification zone 10 is derived from an ethanol esterification zone, distillation zone 50, along with the recycle of 500 parts per hour from a distillation zone 18. The reaction effluent from zone 10 enters distillation zone 18, in which there is distilled, at a temperature ranging from 40° to 130° C. and at a pressure of 20 psia, as overhead the above-mentioned methanol-methyl acetate azeotrope which is recycled to the esterification reactor via line 20 at the rate of 50 parts per hour. Then 260 parts per hour of methyl acetate product (together with a small amount of water) are taken overhead in a further distillation which is carried out at atmospheric pressure and at temperatures in the range of 50° to 130° C. The bottoms from this distillation, comprising water and acetic acid, are then separated by distillation at a pressure of about 30 psia and at temperatures in the range of 120° C. to 150° C. As a result, the separated water is drained via line 22 and about 500 parts per hour of acetic acid are recycled to esterification zone 10 via lines 24 and 14. The methyl acetate is substantially dehydrated and then fed to carbonylation zone 26 via line 28.

Carbonylation zone 26 comprises a stirred pressure reactor filled with a mixture composed of approximately 93.5 mole % methyl acetate, 2.25 mole % methyl iodide, 4.0 mole % lithium iodide and 0.25 mole % rhodium acetate. This mixture is heated to about 170° C. and carbon monoxide is introduced into the reactor to provide and maintain a partial pressure of carbon monoxide of 300 psi, resulting in a total reactor pressure of about 500 psig. The liquid reaction product is withdrawn through line 40 and distilled to separate a product acetic anhydride stream (42) and to provide recycle streams containing some acetic anhydride as well as unreacted methyl acetate and iodine, lithium and rhodium values resulting from the methyl iodide, lithium iodide and rhodium acetate initially charged, the recycle streams being continuously recycled to the reactor 26. The reaction is carried out so as to provide a residence time in the reactor of about three hours. Thus, there are continuously fed about 750 parts per hour of methyl acetate (including 490 parts of recycled methyl acetate) along with an iodine, lithium and rhodium recycle comprising 18 parts per hour of methyl iodide, 32 parts per hour of lithium iodide and 2 parts per hour of rhodium acetate, together with the recycled acetic anhydride, with the recycle streams forming as described below. The reaction mixture is continuously withdrawn at the rate of 1000 parts per hour and passed into distillation zone 36. In distillation zone 36, the reactor effluent is first flashed at about 50 psia and 150° C. The heavy liquid from the flash, which contains the catalyst components, some methyl acetate and acetic anhydride, is recycled to carbonylation zone 26 at the rate of approximately 300 parts per hour. The vapor from the flash is fractionally distilled at a pressure of about 50 psia and at a temperature in the range of 50° to 160° C. to separate about 440 parts per hour of a "light" fraction comprising methyl acetate and methyl iodide, which is recycled to carbonylation zone 26 via line 34. The bottoms from this distillation is composed of about 260 parts per hour of product acetic anhydride which is fed via line 42 to ethanol esterification zone 44 to react with an ethanol stream 46 from the hydrogenation section.

The ethanol esterification zone 44, which is suitably defined by a tank, is operated at about 100° C. to 100 psia, and into which is fed 260 parts per hour of acetic anhydride via line 42, 260 parts per hour of ethanol (with some unconverted ethyl acetate and aqueous impurities) recycled from the hydrogenation section, (line 46), and recycled acetic anhydride (250 parts per hour) and acetic acid (250 parts per hour) via line 47. The reaction effluent from ethanol esterification zone 44 enters distillation zone 50, in which a first distillation column separates ethyl acetate (260 parts per hour which is passed to hydrogenation zone 54 via line 52) as overhead at atmospheric pressure and at a temperature in the range of 80° C. to 140° C., while a second distillation column, using the bottoms stream of the first distillation column as feed separates out acetic acid (260 parts per hour recycled to first esterification zone 10 via line 14) as overhead, with the bottoms stream being recycled to the ethanol esterification zone 44 via line 47. The second distillation tower operates at about atmospheric pressure and at temperatures in the range of 120° C. to 140° C.

The hydrogenation zone 54, which undertakes a vapor phase reductive reaction with solid copper-chromite as the catalyst, is operated at about 250° C. and 400 psig and is fed with 260 parts per hour of ethyl acetate via line 52 along with slightly more hydrogen from line 56. With recycling, the hydrogen to ethyl acetate ratio in the reaction zone 54 is greater than 10. The reaction effluent from the hydrogenation zone 54 enters distillation zone 62 in which 260 parts of ethanol are withdrawn in the column bottoms as product, while 260 parts of ethanol containing some unconverted ethyl acetate is separated in the overhead and recycled via line 46 to ethanol esterification zone 44.

The slight yield loss in the reaction and distillation zones as well as byproducts of acetic anhydride and/or acetic acid etc. can be compensated by employing a larger production rate in the carbonylation reaction zone, esterification reaction zone, etc. It can be seen that the process is effectively operated using only carbon monoxide, methanol and hydrogen as feed materials.

I claim:

1. A process for the preparation of ethanol from methanol, carbon monoxide and hydrogen feedstocks, comprising the steps of
   (a) reacting methanol and acetic acid in a first esterification zone to form methyl acetate;
   (b) reacting the formed methyl acetate with carbon monoxide in a carbonylation zone to form acetic anhydride;
   (c) reacting the formed acetic anhydride with at least one lower aliphatic alcohol in a substantially anhydrous second esterification zone to form the corresponding lower aliphatic acetates and acetic acid;
   (d) reacting the formed lower aliphatic acetates with hydrogen in a substantially anhydrous hydrogenation zone to form both ethanol and also the corresponding aliphatic alcohols from the acetates;
   (e) separating the formed alcohol into a first ethanol product stream and a second stream comprising the formed corresponding aliphatic alcohols; and
   (f) recycling the second stream to the second esterification zone.

2. A process as claimed in claim 1 wherein the acetic acid reactant in the first esterification zone is formed as a product in the second esterification zone and recycled to the first esterification zone.

3. A process as claimed in claim 1 wherein at least one lower aliphatic alcohol is ethanol.

4. A process as claimed in claim 1 wherein the corresponding lower aliphatic acetate mixture is ethyl acetate.

5. A process as claimed in claim 1 wherein the formed corresponding aliphatic alcohol second stream recycled to the second esterification zone is ethanol.

6. A process as claimed in claim 1 wherein the process is run continuously.

7. A process as claimed in claim 1 wherein the lower aliphatic alcohol is selected from methanol, ethanol and propanol.

* * * * *